(12) United States Patent
Snaper

(10) Patent No.: US 10,994,124 B1
(45) Date of Patent: May 4, 2021

(54) EXTERNAL DEFIBRILLATOR APPARATUS WITH SELF-CONTAINED PIEZOELECTRIC POWER SOURCE

(71) Applicant: Alvin A. Snaper, Las Vegas, NV (US)

(72) Inventor: Alvin A. Snaper, Las Vegas, NV (US)

(*) Notice: Subject to any disclaimer, the term of this patent is extended or adjusted under 35 U.S.C. 154(b) by 141 days.

(21) Appl. No.: 16/050,557

(22) Filed: Jul. 31, 2018

Related U.S. Application Data

(60) Provisional application No. 62/596,330, filed on Dec. 8, 2017.

(51) Int. Cl.
  *A61N 1/38* (2006.01)
  *A61N 1/04* (2006.01)
  *A61N 1/39* (2006.01)

(52) U.S. Cl.
  CPC .......... *A61N 1/046* (2013.01); *A61N 1/0472* (2013.01); *A61N 1/39* (2013.01)

(58) Field of Classification Search
  CPC . A61N 1/046; A61N 1/39; A61N 1/04; A61N 1/3904; A61N 1/39044; A61N 1/38; A61N 1/385
  See application file for complete search history.

(56) References Cited

U.S. PATENT DOCUMENTS

| | | | | |
|---|---|---|---|---|
| 4,608,508 A | * | 8/1986 | Ohnishi ................. | F23Q 3/002 310/339 |
| 5,591,218 A | * | 1/1997 | Jacobson ............. | A61N 1/3704 128/908 |
| 2003/0045905 A1 | * | 3/2003 | Daynes ................. | A61N 1/046 607/5 |
| 2005/0288716 A1 | * | 12/2005 | Zsigmond ............. | A61N 1/378 607/5 |
| 2009/0192559 A1 | * | 7/2009 | Miller ..................... | A61N 1/39 607/5 |
| 2014/0288574 A1 | * | 9/2014 | Abramov ............. | A61N 1/0504 606/129 |
| 2015/0153144 A1 | * | 6/2015 | Cheatham, III ..... | A61N 1/3987 607/7 |
| 2016/0287860 A1 | * | 10/2016 | Freeman ............. | A61H 31/007 |
| 2018/0036546 A1 | * | 2/2018 | Gross .................. | A61B 5/0422 |

* cited by examiner

*Primary Examiner* — Allen Porter
*Assistant Examiner* — Adreanne A. Arnold
(74) *Attorney, Agent, or Firm* — Ralph E. Jocke; Walker & Jocke

(57) ABSTRACT

An external defibrillator apparatus (10, 74) operates to deliver electrical shocks to the heart muscles of a patient using a self-contained piezoelectric power source. The apparatus has a body (12) which includes a handle portion (26) in fixed operative connection with disposed paddle portions (14, 16). Each paddle portion includes a respective electrode (22, 24). Manual movement of a trigger (28, 78) is operative to cause circuitry (32, 82) which includes a piezoelectric crystal (34) to develop sufficient electrical potential between the electrodes to deliver the electrical shocks to the heart muscles through external contact with the patient's chest.

25 Claims, 10 Drawing Sheets

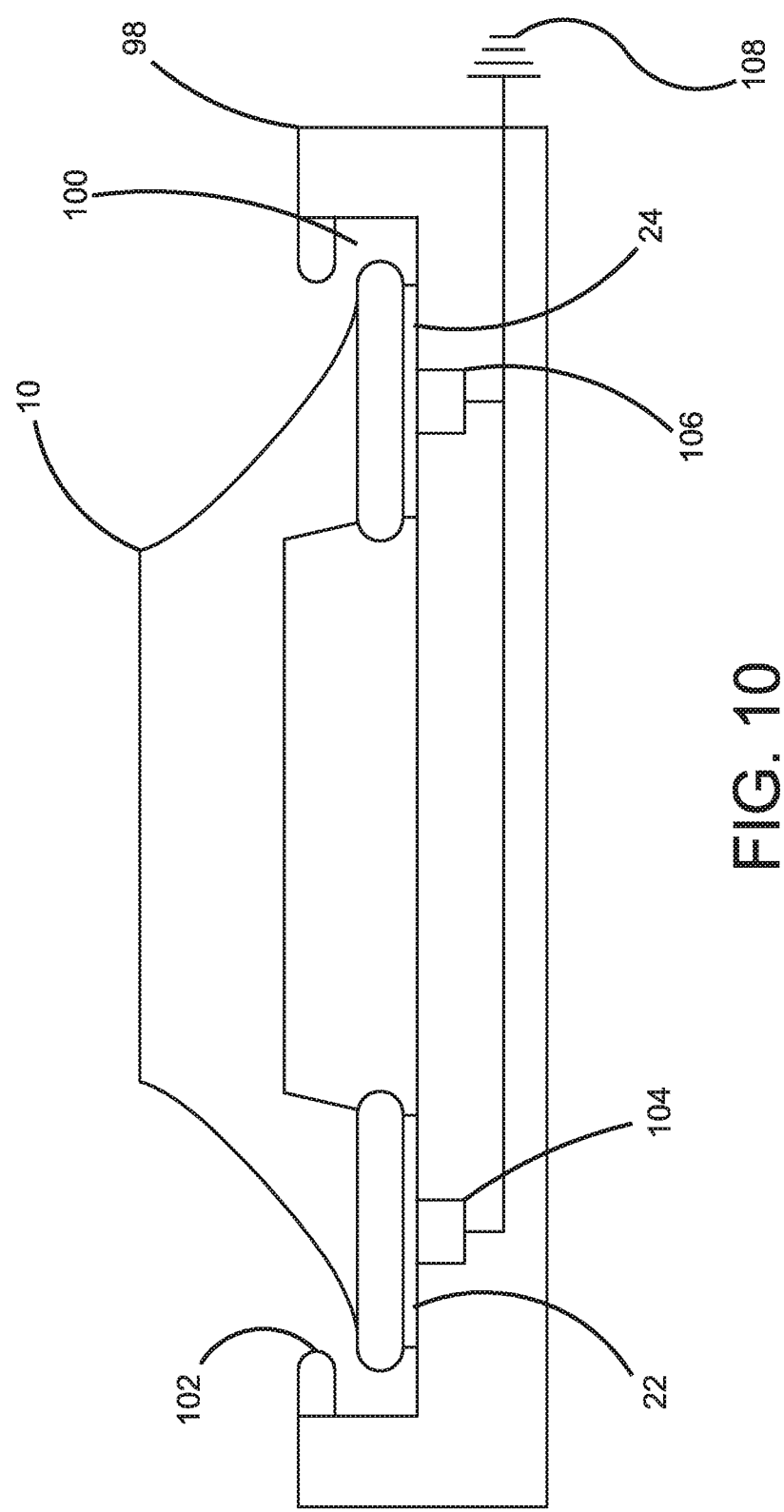

EXTERNAL DEFIBRILLATOR APPARATUS WITH SELF-CONTAINED PIEZOELECTRIC POWER SOURCE

TECHNICAL FIELD

The exemplary embodiments relate to a defibrillator apparatus. The exemplary defibrillator embodiments provide an external defibrillator apparatus with improved operational characteristics.

BACKGROUND

Myocardial infarction which is also commonly referred to as a heart attack, is a common medical problem. Published statistics indicate that in the United States a person suffers a heart attack every 43 seconds.

When a heart attack occurs it is important to treat the individual as soon as possible to attempt to restore the heart's blood pumping function. In order to provide treatment more quickly external defibrillators are being deployed in increasing numbers of public and private facilities. These defibrillators can be used to provide a shock to the heart muscles that will restart a stopped heart and/or restore proper rhythm to a heart that is experiencing ventricular fibrillation. These external defibrillators can often be operated by persons with very limited training to provide medical assistance as soon as possible after a heart attack occurs.

Available external defibrillator units have a relatively high cost. The relatively high cost limits where such units are deployed. Such units also require maintenance. Maintenance commonly includes periodic replacement of the batteries that are needed for operation of the unit. Some defibrillators can also be bulky and may be difficult to transport to the patient, manipulate and properly use.

External defibrillator apparatus may benefit from improvements.

SUMMARY OF DISCLOSURE

Exemplary embodiments relate to an external defibrillator apparatus that operates using a self-contained piezoelectric power source. Exemplary embodiments provide a small and lightweight unit that is easier to transport and to use. Defibrillator apparatus of exemplary embodiments have an unlimited storage life and do not require periodic maintenance. The apparatus of exemplary embodiments also provides improved performance and can be produced at a lower cost compared to conventional devices.

BRIEF DESCRIPTION OF DRAWINGS

FIG. 10 is a side schematic view of the defibrillator apparatus in connection with the docking station.

DETAILED DESCRIPTION OF EXEMPLARY EMBODIMENTS

Figure 1:
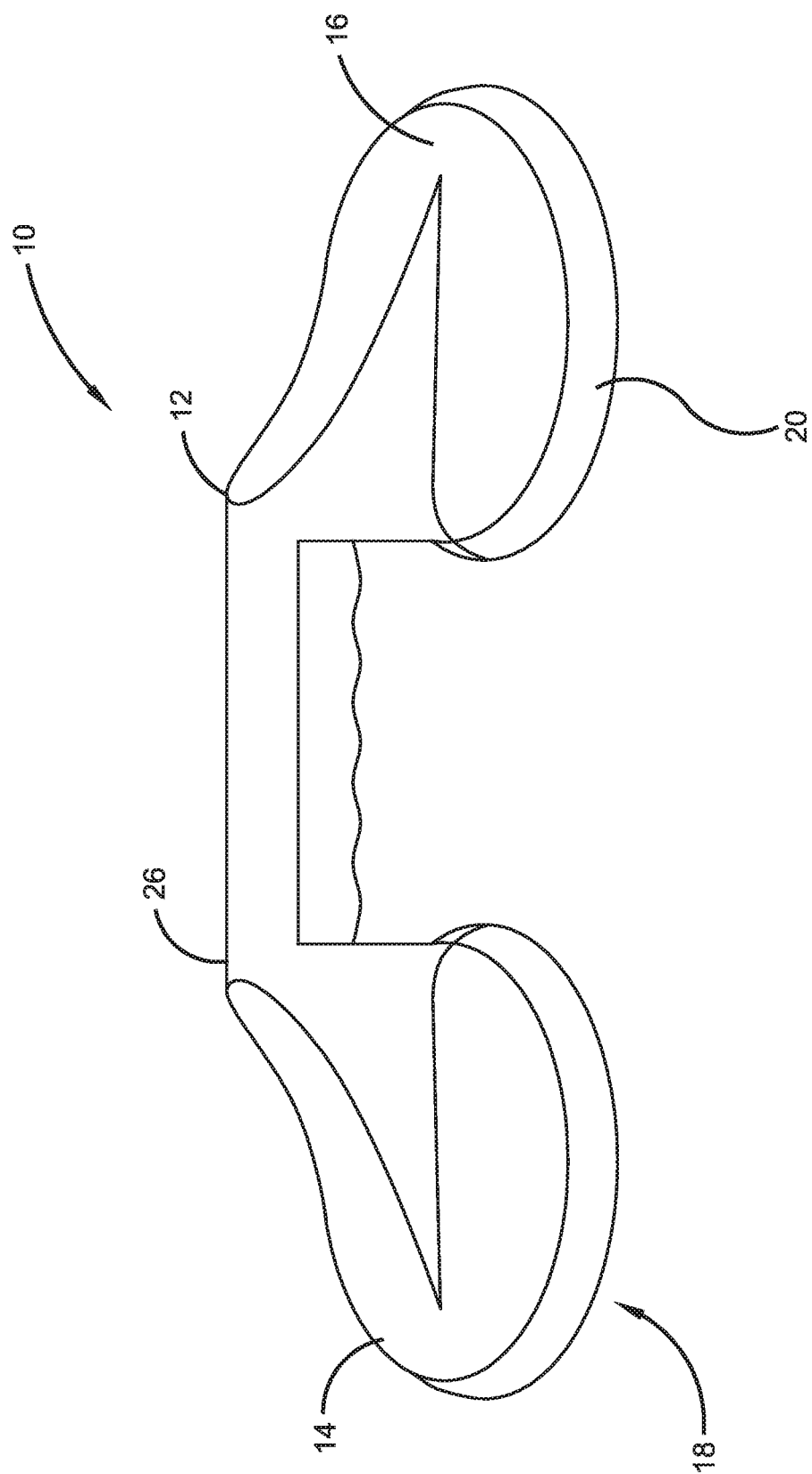
FIG. 1 is a perspective view of an exemplary embodiment of a defibrillator apparatus.

Referring now to the drawings and particularly to FIG. 1 there is shown therein an exemplary defibrillator apparatus 10. The exemplary apparatus 10 includes a body 12. Body 12 of the exemplary embodiment is comprised of a unitary body of a generally rigid plastic or other suitable material. The exemplary body includes disk shaped paddle portions 14, 16. Each panel portion includes a generally circular flat face 18, 20. Each flat face has in mounted connection therewith a respective circular electrode 22, 24. In the exemplary embodiment the electrodes are comprised of electrically conductive metal material that is suitable for transmitting an electrical shock to heart muscles through the skin of the patient.

Figure 2:
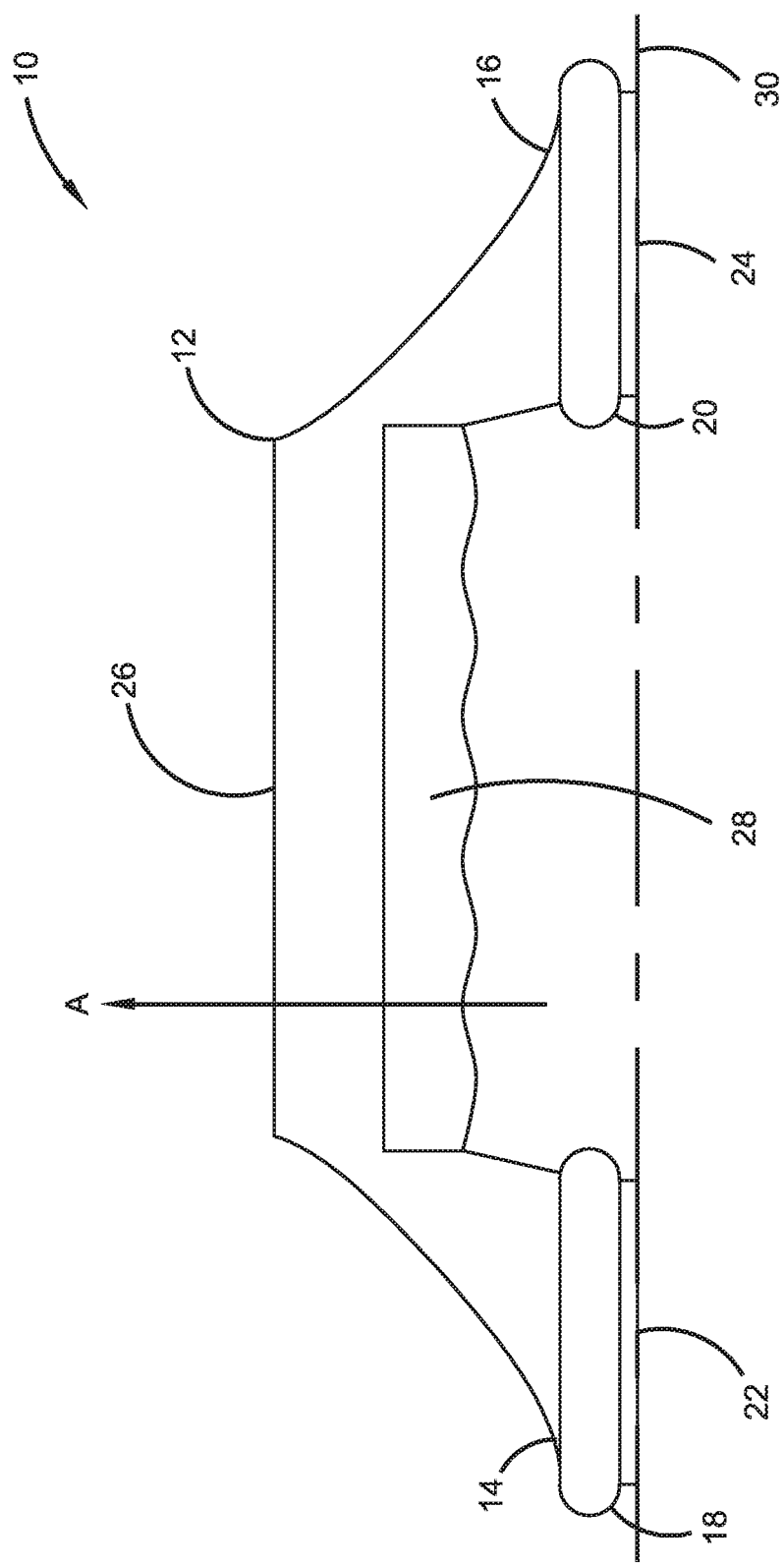
FIG. 2 is a side view of the apparatus shown in FIG. 1.

The exemplary body 12 further includes a handle portion 26. The handle portion extends intermediate of the paddle portions and provides a rigid connection between the paddle portions 14, 16. The handle portion also provides for the electrodes 22, 24 to be disposed apart at a fixed distance. Movably mounted in operative connection with the handle portion 26 is a trigger 28. In the exemplary arrangement the trigger 28 is movable relative to the handle portion through manual squeezing action of the handle. As represented in FIG. 2 the electrodes extend in a common plane 30. In the exemplary embodiment shown in FIG. 2 the trigger 28 is moved relative to the handle along an actuation direction perpendicular to the common plane 30 in the direction of arrow A to cause an electrical potential to be applied across the electrodes so as to deliver a shock to the heart muscles when the electrodes are in contact with the chest of the patient. Of course it should be understood that this approach is exemplary in other embodiments other approaches may be used.

Figure 3:
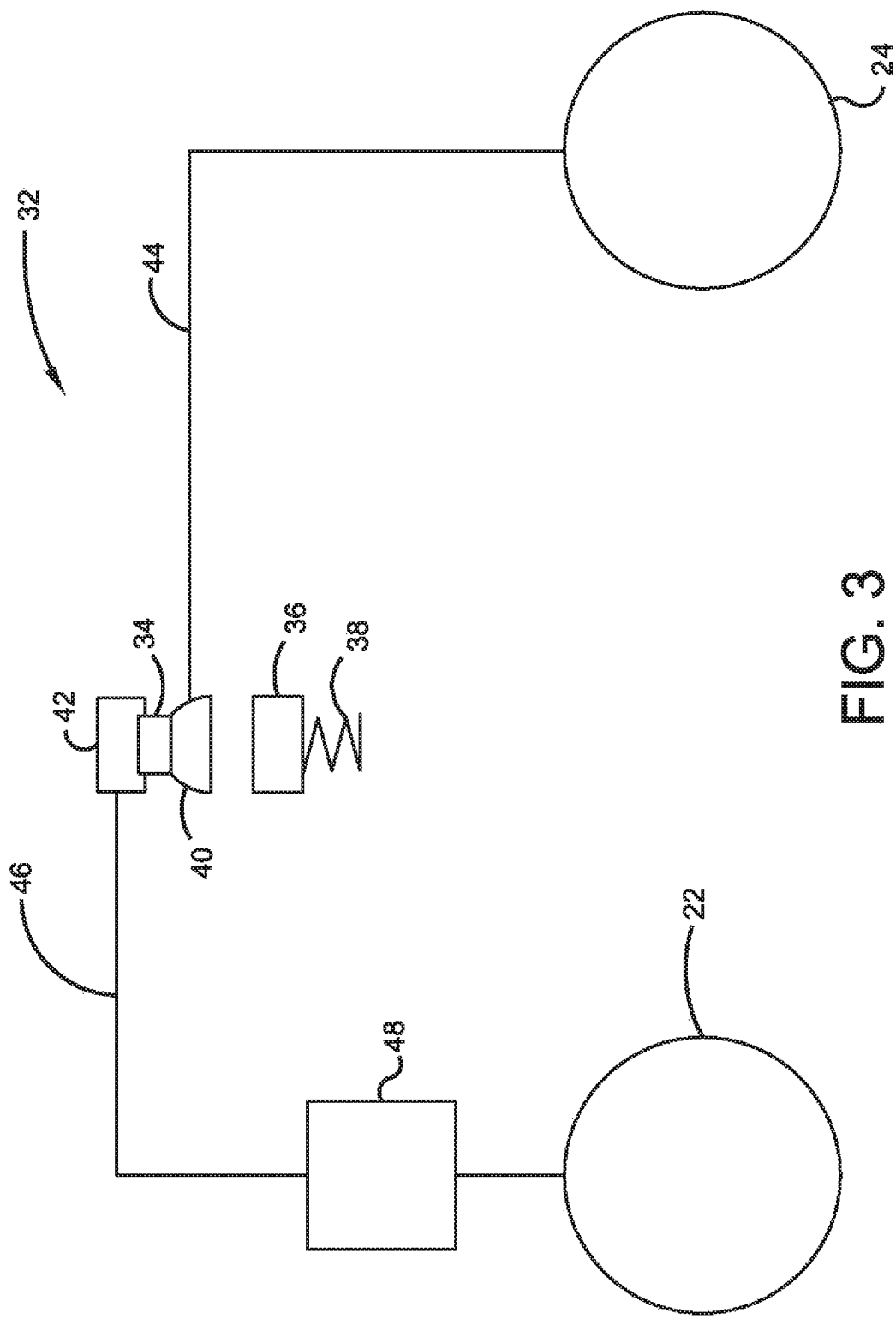
FIG. 3 is a schematic view of a circuit used in an exemplary embodiment.

FIG. 3 shows an electrical schematic of circuitry 32 associated with an exemplary defibrillator apparatus. The circuitry 32 is also alternatively referred to herein as a circuit. The exemplary circuitry includes a piezoelectric crystal 34. The crystal 34 is operative to produce an electrical potential in response to an impact strike force acting on the crystal. In the exemplary arrangement the apparatus includes a movable hammer 36 which is shown schematically in FIG. 3. The hammer is movably mounted in operative connection with the body and is movable in response to force provided by a biasing member such as a hammer spring 38, to cause the hammer to impact an impact pad 40 which is in contact with the crystal 34. The exemplary impact pad 40 is comprised of electrically conductive material. A base 42 comprised of electrically conductive material is in contact with the crystal 34 on an opposed side from the impact pad 40. As shown in FIG. 3 the impact pad 40 is in electrical connection with electrode 24 through an electrical conductor 44. The base 42 is in electrical connection with electrode 22 through an electrical conductor 46.

In the exemplary arrangement shown at least one electrical component 48 is electrically connected intermediate of the base 42 and electrode 22. In some exemplary arrangements electrical component 48 may include one or more diodes so as to assure that current can only flow in one direction through the electrical conduit 46. Such diodes may be used in exemplary embodiments to assure that current flow from the deformation of the crystal is transmitted to the electrodes, while current flow in an opposed direction as the crystal recovers and returns to its original configuration is not transmitted to the electrodes. In other arrangements the component 48 may include one or more resistors or other items that limit or control the flow of electricity through the conduit 46. Other arrangements may include other or additional circuit structures that provide the desired electrical potential between the electrodes for purposes of providing shocks for restarting or imparting appropriate rhythm to heart muscles.

In exemplary arrangements, the trigger 28 is in operative connection with the hammer 36. Movement of the trigger is operative to cause the hammer to impart an impact strike to the crystal 34. The force of the impact strike on the crystal is operative to produce an instantaneous electrical potential which is transmitted to the respective electrodes 22, 24. When the electrodes are pressed against the chest of the patient (the chest contact areas corresponding to plane 30 in the areas of the electrodes), the electrodes impart a shock to the heart muscles through the skin of the patient which is generally sufficient to cause muscle contractions in a manner that will reinstate proper heart function. In exemplary arrangements this may include restarting muscle contractions or providing proper contraction rhythm when the heart is in ventricular fibrillation which does not cause proper blood pumping function. In exemplary arrangements the piezoelectric crystal may be comprised of lead ziconate titanate (PZT). However in other embodiments other crystal materials may be used.

Figure 4:
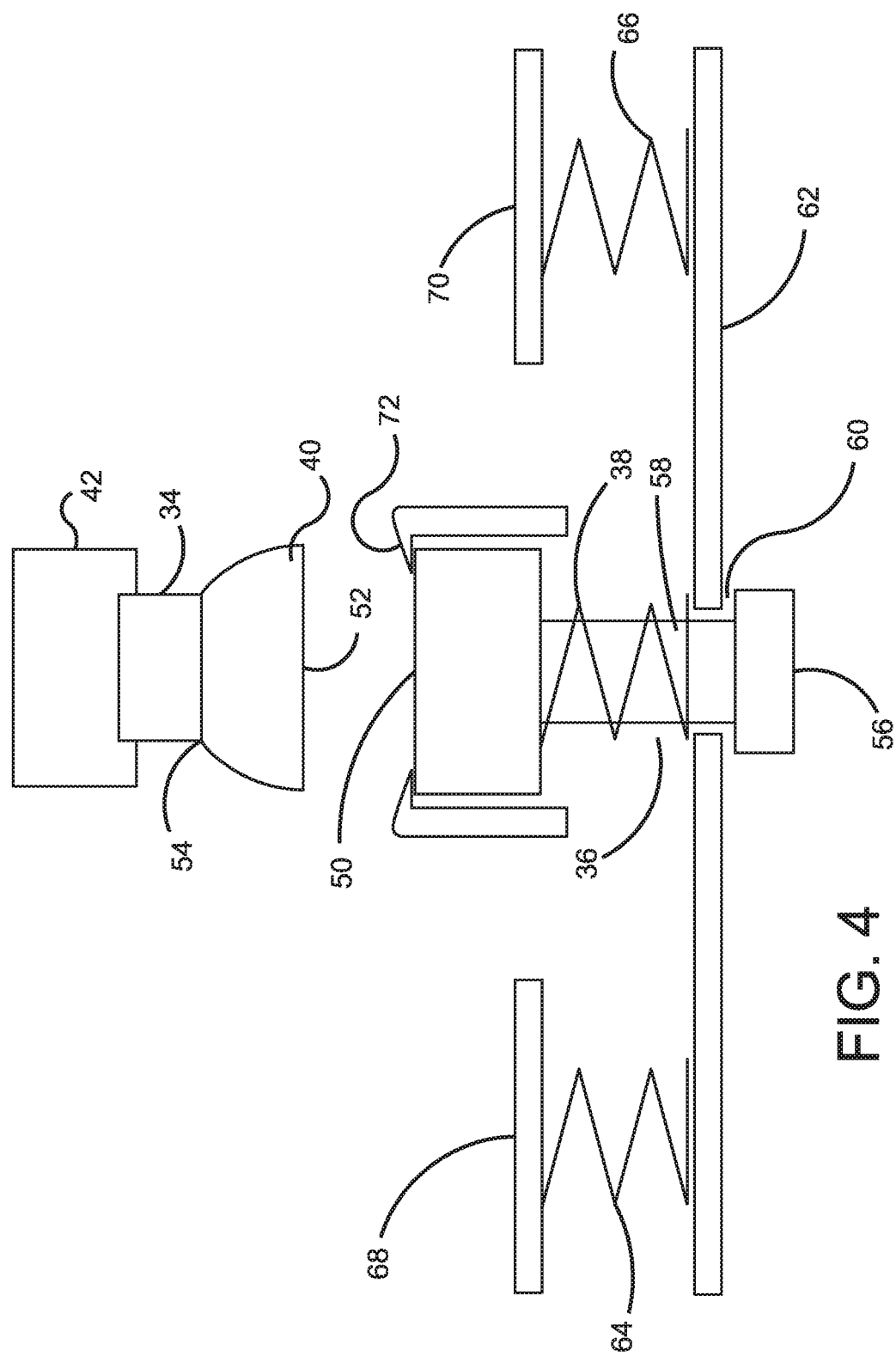
FIG. 4 is a schematic view of an exemplary electrical power generating device.

FIG. 4 shows schematically an exemplary structure used in connection with piezoelectric crystal 34 to impart an impact strike thereto so that the crystal produces the desired electrical potential. As represented in FIG. 4 exemplary hammer 36 includes a head 50. In the exemplary embodiment the head 50 of hammer 36 generally corresponds in surface area to a backside 52 of impact pad 40. In the exemplary arrangement the impact pad 40 includes a nose 54 on the side of the impact pad that is opposed of the backside 52. The nose 54 of the exemplary embodiment has a smaller surface area than the backside. The nose 54 is immediately adjacent to and in contact with the crystal 34. In the exemplary embodiment the nose is operative to concentrate the force of the imparted strike from the hammer onto the surface of the crystal. Of course it should be understood that this structure is exemplary and in other embodiments other arrangements may be used.

The exemplary hammer 36 further includes a retract button 56. The retract button 56 extends on the hammer 36 at an end opposed of the head 50. A stem 58 extends longitudinally between the head 50 and the retract button 56. In the exemplary embodiment the stem 58 has a diameter smaller than each of the head 50 and the retract button 56. The hammer spring 38 extends in surrounding relation of the stem 58 as shown.

In the exemplary arrangement the stem 58 extends through an opening 60 in a retract bar 62. The retract bar is biased in a downward direction as shown in FIG. 4 by retract springs 64, 66. Retract springs 64 and 66 act to provide a biasing force between retract bar 62 and surfaces 68, 70. In exemplary arrangement surfaces 68, 70 are stationary surfaces within the body of the apparatus.

In the exemplary arrangement the head 50 of the hammer 36 is releasably engageable with at least one hammer catch 72. In the exemplary embodiment the hammer catch comprises at least one inwardly directed deformable cross-sectional finger that is operative to engage and hold the hammer by the head 50 in a stationary position until a spring force biasing the hammer head 50 toward the impact pad 40 reaches a force level. When the force level is reached or exceeded the hammer catch 72 deforms and enables the hammer head 50 to move so as to contact the backside 52 of the impact pad 40 and impart an impact strike to the crystal 34.

In exemplary arrangements, when electrical energy is to be produced by the defibrillator apparatus the hammer 36 is positioned so that the head 50 is held stationary in engagement with the hammer catch 72. Movement of the trigger 28 along the actuating direction is operative to cause movement of the retract bar 62 in an upward direction as represented in FIG. 4. Movement of the retract bar 62 by the trigger 28 is operative to compress the retract springs 64 and 66. Such movement is also operative to compress the hammer spring 38. The hammer spring is further compressed by movement of the retract bar 62 toward the head 50 of the hammer 36 as shown.

When the force of the hammer spring 38 reaches the level at which the hammer catch 72 no longer will hold the head 50 stationary, the hammer catch 72 deforms and releases the hammer 36 to move. The hammer 36 moves in response to the biasing force of the hammer spring 38 acting against the head 50. The head 50 moves rapidly in the longitudinal direction to provide an impact contact with the backside 52 of the impact pad 40. The hammer engagement with the impact pad imparts an impact strike on the crystal 34 which produces an immediate high electrical potential across the opposed sides of the crystal. The electrical potential is transmitted to the electrodes 22, 24 so as to provide the shock to the heart muscles of the patient.

In the exemplary arrangement once the hammer has contacted the impact pad, manually releasing the trigger 28 is operative to cause the retract bar 62 to move downwardly as represented in FIG. 4 in response to the biasing force of the retract springs 64, 66. The retract bar also operatively engages the retract button 56 of the hammer 36 so as to move the hammer in a longitudinal direction away from engagement with the impact pad 40. Movement of the head 50 of the trigger 36 away from the impact pad responsive to movement of the retract bar 62 eventually causes the head to again engage with the hammer catch 72. Once the head 50 has engaged the hammer catch 72 another electrical shock can be produced using the apparatus by movement of the trigger 28. Of course it should be understood that the structure for generating the electrical potential is exemplary and other embodiments may use other arrangements. Such arrangements may use for example, multiple crystals, other hammer configurations and different features.

As can be appreciated this exemplary approach is usable to provide an essentially unlimited number of electrical shocks so as to revive the patient. Further there is no risk that electrical power sufficient for providing the shock to the patient will not be available due to insufficient battery power or excess battery draw as may occur with other types of defibrillator apparatus. Further the exemplary arrangement is fully self-contained, lightweight and easy to maneuver into contacting position with the chest of the patient. The electrodes are also provided at a fixed spacing so that they can be properly oriented easily in proper contact with the chest of the patient. Numerous other advantageous features of the exemplary embodiment will be apparent to those having knowledge in the field.

Figure 5:
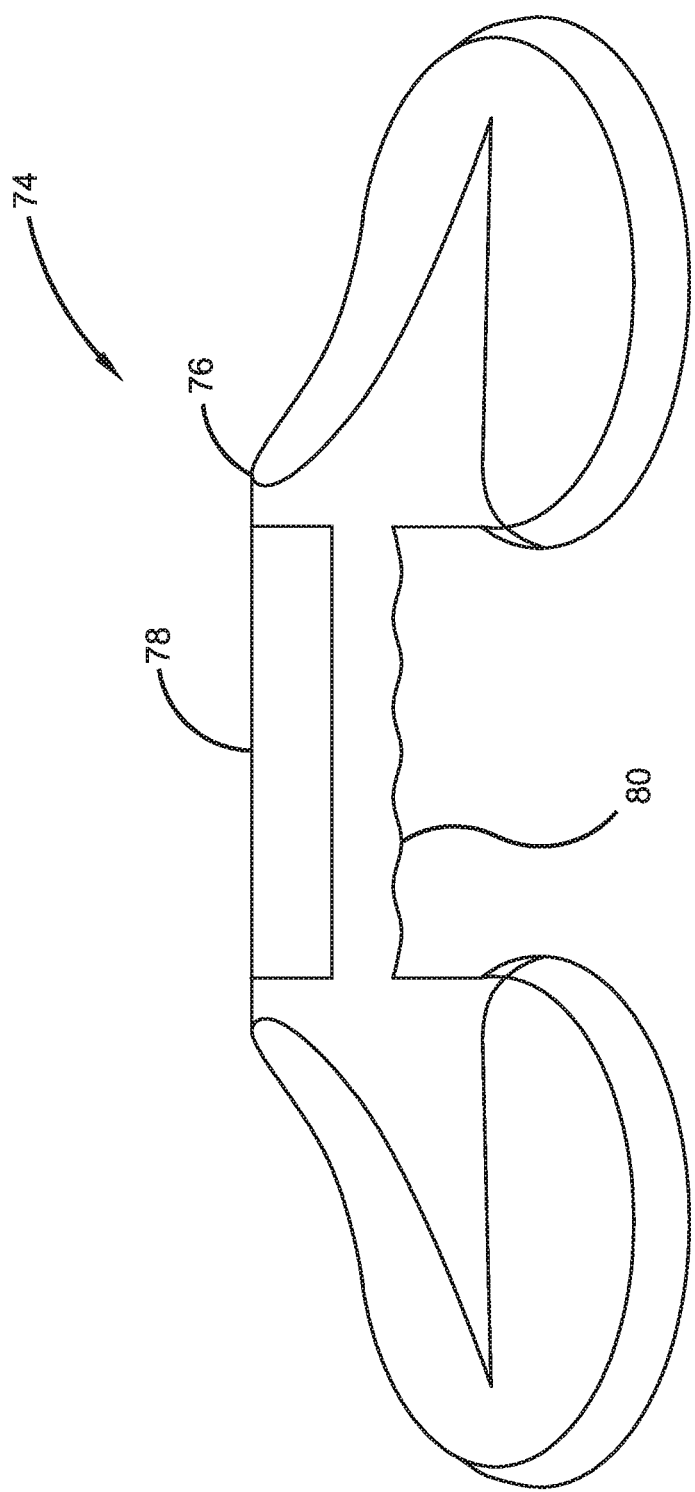
FIG. 5 is a perspective view of an alternative embodiment of a defibrillator apparatus.

FIG. 5 shows an alternative embodiment of an exemplary defibrillator apparatus 74. Defibrillator apparatus 74 has a body 76 that includes features generally similar to those described in connection with apparatus 10. Apparatus 74 differs in that it includes a trigger 78 which is movable relative to a handle portion 80 in a relatively inward direction toward the plane of the electrodes to generate the electrical potential.

Figure 6:
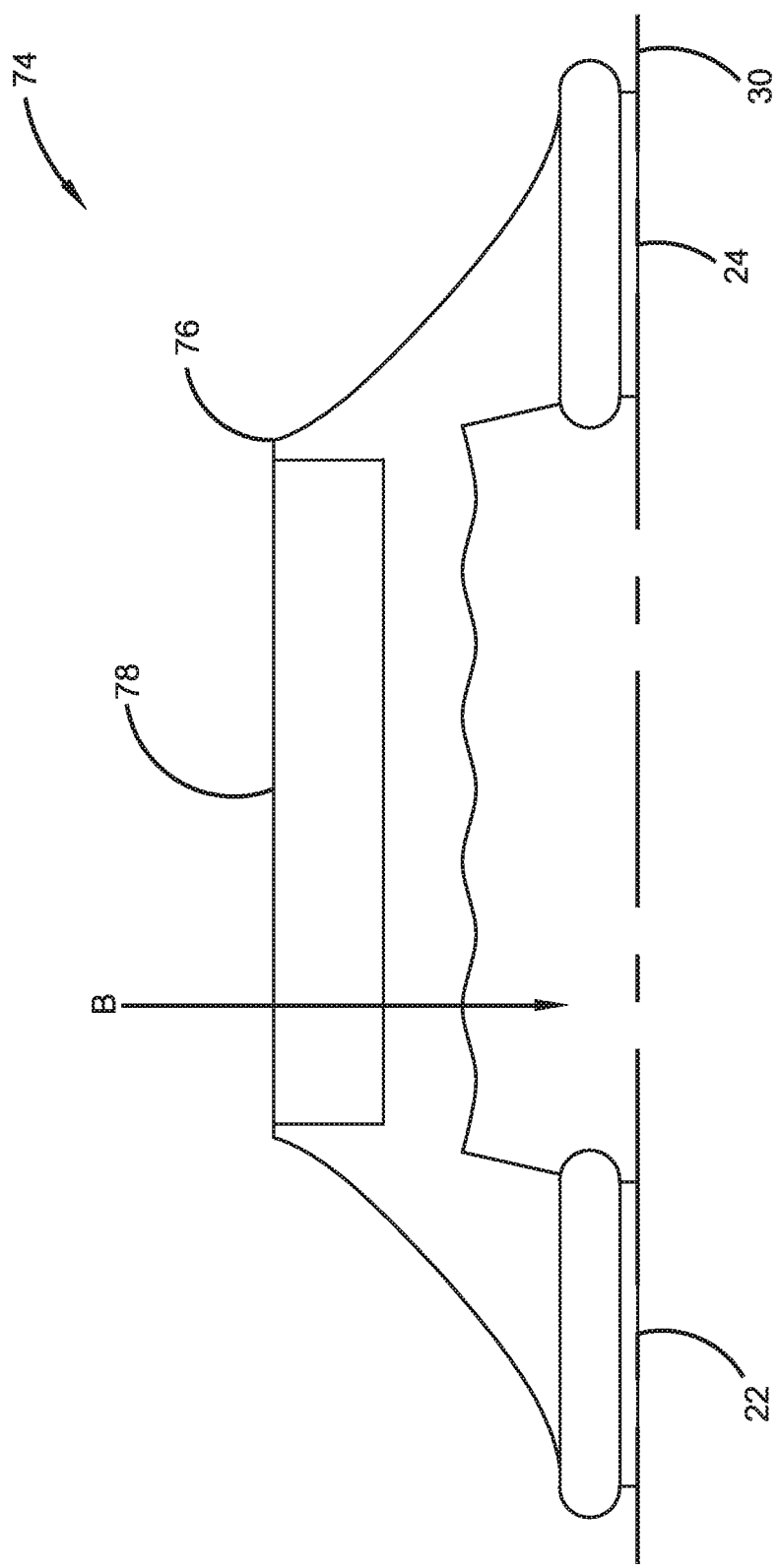
FIG. 6 is a side view of the alternative embodiment shown in FIG. 5.

The defibrillator apparatus of FIG. 5 operates to provide the electrical shock responsive to movement of the trigger 78 along an actuation direction perpendicular to the common plane 30 of the electrodes 22, 24 represented by Arrow B in FIG. 6. However unlike the apparatus 10 in which the trigger moves away from the plane along the actuation direction to provide the electrical shock, apparatus 74 is configured to provide the shock responsive to movement of the trigger 78 along the actuation direction toward the plane of the electrodes. Thus in this exemplary embodiment the defibrillator apparatus 74 is operated by pressing the body 76 and the electrodes against the chest of the patient and pushing the trigger 78 inward. This configuration may present advantages in some exemplary arrangements by assuring that the electrodes are pressed firmly against the chest of the patient when the shock is generated. Of course this approach is exemplary and other embodiments other approaches may be used.

Figure 7:
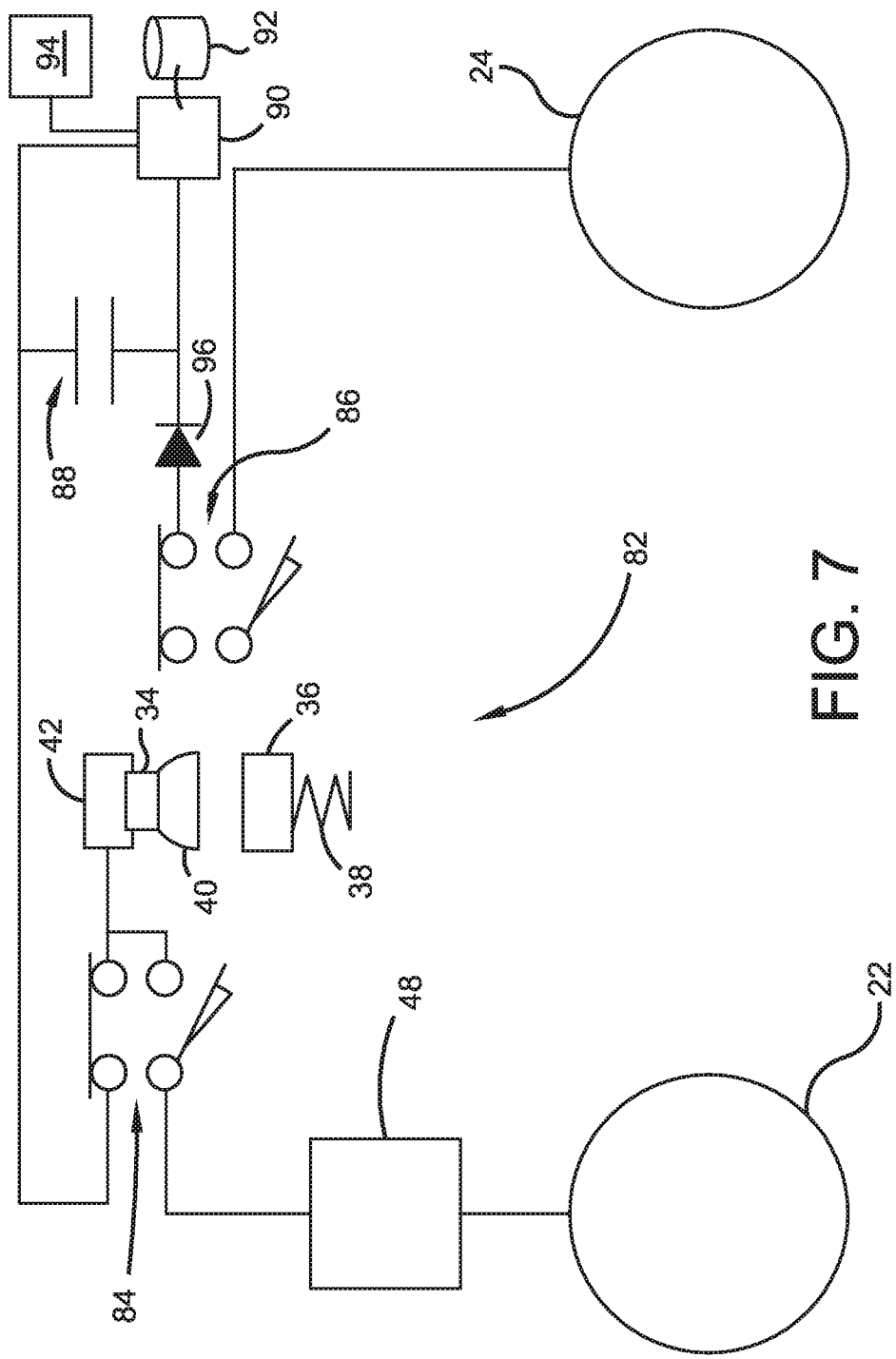
FIG. 7 is a schematic view of a circuit used in alternative embodiments in a first circuit condition.
Figure 8:
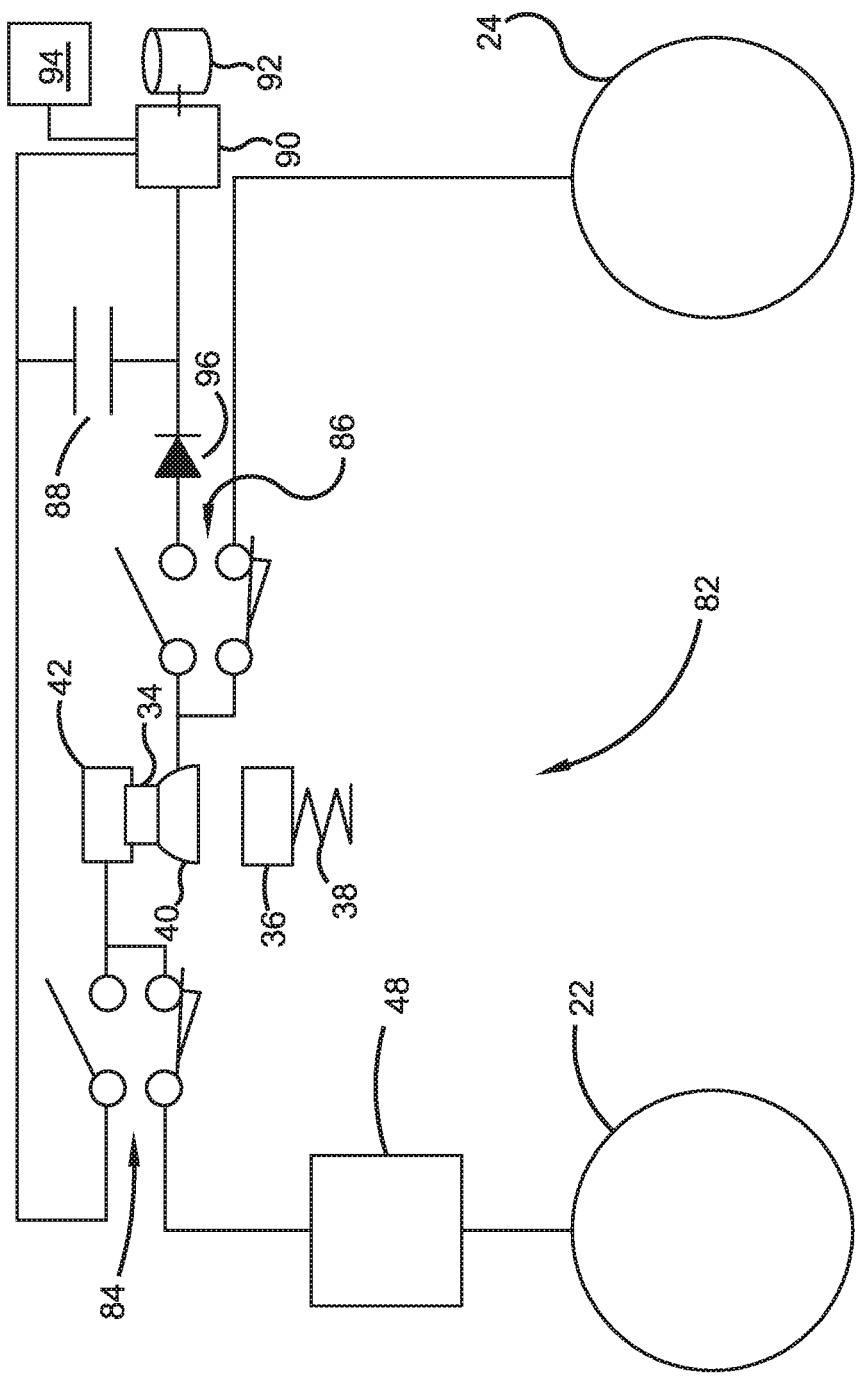
FIG. 8 is a schematic view of the circuit shown in FIG. 7 in a second circuit condition.

Exemplary embodiments may also include other or additional features to facilitate operation of the defibrillator apparatus. FIGS. 7 and 8 schematically show circuitry 82 which may be used in alternative embodiments to provide additional features and capabilities for the defibrillator apparatus. Circuitry 82 may be referred to herein as a circuit. Exemplary circuitry 82 includes the elements of the circuitry 32 previously discussed for purposes of selectively providing an electrical shock to the patient through the electrodes 22, 24. In addition circuitry 82 includes switches 84, 86. Switches 84,86 may be selectively configured to enable the electrical potential produced by piezoelectric crystal 34 to be utilized as a power source for other electrical components in circuitry 82 at selected times when power is not fully utilized for providing a shock to the patient.

Exemplary circuitry 82 includes at least one capacitor 88. Capacitor 88 is operative to store electrical power that can be utilized by other elements of circuitry 82. In the exemplary embodiment such other elements include a processor 90. Processor 90 is an operative connection with a data store 92. An indicator 94 is in operative connection with the processor 90, the data store 92 as well as the capacitor 88. Exemplary circuitry 82 further includes diodes 96 or other suitable circuit structures to provide the controlled desired delivery of the electrical power to the processor, data store, indicator and other circuit components.

In exemplary arrangements the processor may include a processor suitable for carrying out computer executable instructions that are stored in the one or more associated data stores 92. The processor may include or be in connection with a nonvolatile storage medium including non-transitory instructions that include a basic input/output system (BIOS). For example, the processor may correspond to one or more of a combination of a CPU, FPGA, ASIC or other integrated circuit or other type of circuit that is capable of processing data and instructions. The data store or data stores may correspond to one or more of volatile or nonvolatile memories such as random access memory, flash memory, magnetic memory, optical memory, solid-state memory or other devices that comprise a non-transitory medium that are operative to store y processor executable instructions and data. Processor executable instructions may include instructions in any of a plurality of programming languages and formats including, without limitation, routines, subroutines, programs, threads of execution, objects, methodologies and functions which carry out the actions such as those described herein. Structures for processors may include, correspond to and utilize the principles described in the textbook entitled Microprocessor Architecture, Programming, and Applications with the 8085 by Ramesh S. Gaonker (Prentice Hall, 2002) which is incorporated herein by reference in its entirety.

Exemplary processors may include those produced by Intel Corporation, Advanced Micro Devices and other types of processors. Exemplary data stores used in connection with exemplary embodiments may include any one or more of several types of tangible media suitable for holding computer executable instructions. These may include for example, magnetic media, optical media, solid-state media or other types of media such as RAM, ROM, PROMs, flash memory, computer hard drives or any other form of media suitable for holding data and computer executable instructions. Exemplary circuitry may also include exemplary hardware and software interfaces for communication between the components of the circuitry.

In exemplary arrangements the exemplary data store 92 includes processor executable instructions that are operative to cause the processor 90 to determine if electrical signals generated by the heart muscles of a patient that can be sensed through electrodes 22, 24 in contact with the patient's chest, correspond to a condition of the patient which requires a shock to restore proper heart function. In exemplary arrangements the processor executable instructions enable the processor to make a determination if the electrical signals detected from a patient through chest contact with the electrodes correspond to a condition in which the heart of the patient is in a stopped condition or is in a ventricular fibrillation condition. The exemplary processor executable instructions further enable the processor to output signals responsive to such a determination to provide an indication through the indicator 94 of such determination. For example in some arrangements the indicator 94 may be a low-power display such as an OLED display which can output indicia such as text or graphics that can be visually read by an operator of the defibrillator apparatus. In exemplary arrangements the processor executable instructions may be operative responsive to the determination to provide an indication of the determined condition and/or instructions to the operator and how to use the device to provide the needed shock to the heart muscles of the patient.

In an exemplary arrangement the switches 84, 86 may be in the positions shown in FIG. 7 responsive to the device not being in contact with the chest of the patient. In some exemplary arrangements the switches may be actuated to be in the condition shown in FIG. 7 when the flat faces 18, 20 of the body are not pressed firmly against a surface such as the chest of the patient. For example in some arrangements switches 84 and 86 may be an operative connection with a pressure contact switch actuator so as to be in the position shown in FIG. 7 when contact pressure below a threshold is applied at the flat faces which support the electrodes. Of course in other embodiments other switching arrangements may be used.

In the condition of the circuitry 82 shown in FIG. 7 actuation of the trigger of the defibrillator apparatus is operative to produce electrical power that is directed to the capacitor 88. The capacitor is charged through one or more actuation cycles of the trigger which operate in each cycle to cause the crystal 34 to produce electrical power. In exemplary arrangements electrical power collected at the capacitor 88 may be utilized by the processor 90 operating in accordance with the instructions stored in the data store 92 to provide an output through the indicator 94 that the circuitry is operational.

Once sufficient power is available at the capacitor 88 for the processor to operate, the instructions provided to the indicator may instruct the user of the device on positioning the electrodes 22, 24 against the chest of the patient for purposes of detecting the electrical signals corresponding to the current muscle activity of the heart. The processor 90 may then operate in accordance with its programming to detect the electrical signals corresponding to the heart muscle activity that are received through the electrodes. The processor 90 operates in accordance with the processor executable instructions to make a determination concerning whether the electrical signals received correspond to at least one of a heart stoppage condition or ventricular defibrillation condition. The at least one processor is operative responsive at least in part to making the determination to provide outputs through the indicator 94 which include indicia which informs the user as to the condition detected.

In exemplary embodiments the instructions output through the indicator 94 responsive to the determination may instruct the user on how to position the defibrillator apparatus against the chest of the patient for purposes of providing a shock to attempt to restore proper heart function. In an exemplary arrangement the indicia provided through the indicator may instruct the user to press the electrodes on the paddle portions of the unit in appropriate locations firmly and hard against the patient's chest, and to then move the trigger.

In an exemplary arrangement the pressing of the paddle portions firmly against the patient's chest is operative to provide a force above the threshold and change the condition of the switches 84, 86 from the conditions shown in FIG. 7 to the conditions shown in FIG. 8. In this condition and impact strike imparted to the crystal 34 by movement of the trigger directly applies the electrical power only to the electrodes 22, 24 so that the heart muscles of the patient receive the desired shock. As can be appreciated in this condition as shown in FIG. 8 none of the electrical power generated by the crystal is diverted to the capacitor 88 and other circuit elements. In this condition multiple shocks can be applied to the heart of the patient by repeatedly moving the trigger in the manner previously discussed.

In exemplary arrangements once a shock has been applied to the heart of the patient, the paddle portions of the body 12 can be retracted away from the patient chest or the force level pressing the electrodes against the patient's chest is otherwise dropped below the threshold returning the circuitry to the condition shown in FIG. 7. In this condition the capacitor 88 may be recharged by trigger movement if necessary so that the diagnostic determinations can again be made through operation of the processor 90. In some exemplary arrangements such diagnostic determinations may include placing the electrodes against the patient's chest and the circuitry analyzing the muscle signals to make a determination and provide an indication that proper heart operation has been restored and no further electrical shocks are required. Alternatively, in some embodiments the circuitry responsive to processor executable instructions may make a determination and provide outputs through the indicator 94 of additional steps to be taken such as applying further shocks or other steps that are determined to be appropriate based on the signals received by the processor.

Of course it should be understood that the operation of this exemplary alternative circuitry is described at a high level and only in schematic terms. Exemplary embodiments may include additional features, structures and capabilities suitable for purposes of operation of the particular defibrillator device.

Figure 9:
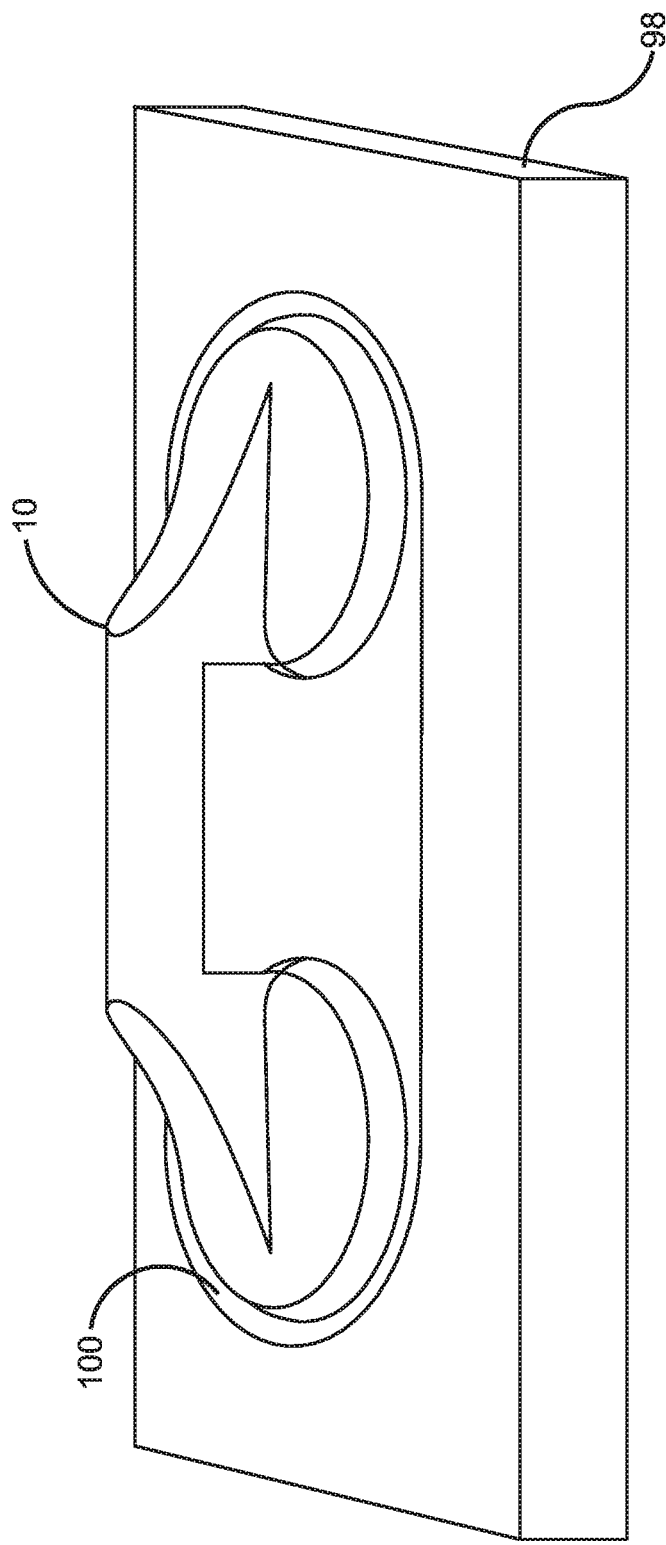
FIG. 9 is a perspective view of an exemplary defibrillator apparatus in connection with a docking station.

In some exemplary arrangements when the defibrillator apparatus is not in use it may be stored in connection with a docking station 98 such as shown in FIGS. 9 and 10. In the exemplary arrangement the docking station 98 includes one or more recesses 100 which are configured to engage the paddle portions of the defibrillator apparatus. Exemplary recesses may include suitable tabs 102 or other structures which operative to hold the defibrillator apparatus and engagement with the docking station. Exemplary docking station 98 may be of a type that is suitable for mounting to vertical or horizontal surfaces as may be necessary to facilitate storage of the device. Of course these arrangements are exemplary.

The exemplary docking station 98 further includes electrical contacts 104, 106. Electrical contacts 104, 106 are configured to be in contacting engagement with the respective electrodes 22, 24 when the defibrillator is in engagement with the docking station. Contacts 104, 106 are in electrical connection with a ground 108 as shown schematically in FIG. 10. This exemplary arrangement provides that any electrical charge that may be present at the electrodes when the defibrillator apparatus is engaged with the docking station is safely discharged. This helps to assure that in the event that the trigger is actuated unintentionally while the apparatus is in the docking station, any electrical charge will be safely dissipated. Of course it should be understood that these approaches are exemplary and other embodiments other approaches may be used.

Thus the exemplary embodiments described herein achieve improved operation, eliminate difficulties encountered in the use of prior devices and systems, and attain the useful results described.

In the foregoing description certain terms have been used for brevity, clarity and understanding. However, no unnecessary limitations are to be implied therefrom because such terms are used for descriptive purposes and are intended to be broadly construed. Moreover, the descriptions and illustrations herein are by way of examples and the inventive features are not limited to the exact features shown and described.

Further in the following claims any feature described as a means for performing a function shall be construed as encompassing any means known to those skilled in the art as being capable of carrying out the recited function and shall not be deemed limited to the particular means shown or described for performing the recited function in the foregoing description or mere equivalents thereof.

The term "non-transitory" with regard to computer readable medium is intended to exclude only the subject matter of a transitory signal per se, where the medium itself is transitory. The term "non-transitory" is not intended to exclude any other form of computer readable media, including, but not limited to, media comprising data that is only temporarily stored or stored in a transitory fashion.

Having described the features, discoveries and principles of the exemplary embodiments, the manner in which such embodiments are constructed and operated, and the advantages and useful results attained; the new and useful structures, devices, elements, arrangements, parts, combinations, systems, equipment, operations, methods, processes and relationships are set forth in the appended claims.

I claim:

1. Apparatus comprising:
   a defibrillator including a body having a handle and a surface and,
a pair of electrodes disposed on the surface, wherein the pair of electrodes are in fixed operative connection with the body,
and each of the electrodes is externally accessible on the body,
a trigger,
wherein the trigger is movably mounted in operative connection with the body,
a hammer,
wherein the hammer is movably mounted in operative connection with the body and wherein the hammer is in operative connection with the trigger,
a circuit,
wherein the circuit includes a piezoelectric crystal,
wherein the circuit is in electrical connection with each of the electrodes,
wherein the trigger, hammer and circuit are within the handle, and
wherein manual movement of the trigger relative to the body is operative to cause the hammer to impart an impact strike to the crystal, wherein the strike is operative to cause the circuit to produce an electrical potential between the electrodes sufficient to provide an electrical shock to heart muscles of a patient through the electrodes, each of the electrodes being in direct engagement with a chest of the patient.

2. The apparatus according to claim 1
wherein the body includes
a pair of disposed paddle portions,
wherein each paddle portion has a respective electrode attached thereto, a handle portion,
wherein the handle portion extends between the paddle portions.

3. The apparatus according to claim 2
wherein the trigger is movably mounted on the handle portion.

4. The apparatus according to claim 3
wherein the electrodes extend in a common plane,
wherein movement of the trigger relative to the body along an actuating direction is operative to cause the strike,
wherein the actuating direction is perpendicular to the plane.

5. The apparatus according to claim 4
wherein manually moving the trigger relative to the body such that the trigger moves away from the plane is operative to cause the strike.

6. The apparatus according to claim 4
wherein manually moving the trigger relative to the body such that the trigger moves toward the plane is operative to cause the strike.

7. The apparatus according to claim 4
wherein the circuit further includes
an impact pad,
a base,
wherein the crystal is positioned intermediate of the impact pad and the base,
wherein the strike is imparted to the crystal by hammer contact with the impact pad.

8. The apparatus according to claim 7
wherein the impact pad includes a backside and a nose,
wherein the nose has a smaller surface area than the backside, wherein when the strike is imparted to the crystal the nose is in contact with the crystal and the backside is in contact with the hammer.

9. The apparatus according to claim 7
wherein the circuit includes,
at least one diode,
wherein the at least one diode is operative to allow electrical flow in the circuit toward one of the pair of electrodes and not in a reverse direction from the one electrode.

10. The apparatus according to claim 7 and further comprising:
a hammer spring,
a hammer catch,
wherein the hammer spring and the hammer catch are each in operative connection with the hammer,
wherein movement of the trigger in a first direction along the actuating direction is operative to cause the hammer spring to be compressed while the hammer is held stationary by engagement with the hammer catch, and
after hammer spring compression, to release the hammer to move under biasing force of the hammer spring to contact the impact pad, whereby the strike is imparted to the crystal.

11. The apparatus according to claim 10 and further comprising:
a retract spring,
wherein the retract spring is in operative connection with the hammer and the trigger,
wherein the retract spring is operative to bias the trigger in a second direction opposed of the first direction along the actuator direction, and is operative to move the hammer away from the impact pad and to cause engagement of the hammer and the hammer catch.

12. The apparatus according to claim 11
wherein the hammer includes
a head,
wherein the head is disposed at a first end of the hammer and is configured to contact the impact pad,
a retract button,
wherein the retract button is disposed at an opposed end of the hammer from the head,
a retract bar,
wherein the retract bar is in operative connection with the retract spring and is operative to move the head away from contact with the impact pad through engagement with the retract button.

13. The apparatus according to claim 10
wherein each paddle portion comprises a respective disc, and each electrode comprises a circular electrode.

14. The apparatus according to claim 13
wherein the handle portion is operative to dispose the electrodes a fixed distance apart.

15. The apparatus according to claim 14
wherein the circuit further includes
a processor,
a processor readable medium including processor executable instructions,
an indicator,
a capacitor,
wherein a further strike is operative to provide power to the capacitor,
wherein the medium includes processor executable instructions operative to determine responsive at least in part to signals detected by the electrodes, at least one of a ventricular fibrillation condition or a heart stopped condition,
wherein the processor is operative responsive at least in part to the determination to cause the indicator to output at least one indication.

16. The apparatus according to claim 4
wherein each paddle portion comprises a respective disc,
wherein each electrode comprises a circular electrode,
wherein the handle portion is operative to dispose the electrodes a fixed distance apart.

17. The apparatus according to claim 1
wherein the circuit includes
at least one diode,
wherein the at least one diode is operative to allow electrical flow in the circuit toward one of the pair of electrodes and not in a reverse direction from the one electrode.

18. Apparatus comprising:
an external defibrillator including
a body, wherein the body includes a handle and a surface,
a trigger,
wherein the trigger is movably mounted in operative connection with the body,
a hammer,
wherein the hammer is movably mounted in operatively supported connection with the body, and wherein the hammer is in operative connection with the trigger,
a circuit,
wherein the circuit includes a piezoelectric crystal,
a pair of electrodes disposed on the surface and in fixed operative connection with the body, wherein each of the electrodes
is configured to contact a chest of a patient,
is in operative connection with the circuit,
wherein the trigger, hammer and circuit are within the handle, and
wherein manual movement of the trigger relative to the body is operative to cause the hammer to impart an impact strike to the crystal,
wherein the impact strike is operative to cause the circuit to produce an electrical potential between the electrodes sufficient to provide an electrical shock to heart muscles of the patient through the pair of electrodes in direct engagement with the chest of the patient.

19. The apparatus according to claim 18
wherein the body includes
a pair of disposed paddle portions,
wherein each paddle portion has a respective electrode operatively attached thereto,
a handle portion,
wherein the handle portion extends intermediate of the paddle portions,
wherein the trigger is movably mounted on the handle portion, wherein the trigger is manually movable.

20. The apparatus according to claim 18
wherein the circuit includes
an impact pad,
wherein the impact pad includes a backside and a nose, wherein the nose has a smaller surface area than the backside,
a base,
wherein the crystal is positioned intermediate of the impact pad and the base,
wherein the nose is in immediately adjacent relation with the crystal,
wherein the impact strike is imparted to the crystal by hammer contact with the backside of the impact pad.

21. The apparatus according to claim 18
wherein the circuit includes,
at least one diode,
wherein the at least one diode is operative to allow electrical flow in the circuit toward one of the pair of electrodes and not in a reverse direction.

22. Apparatus comprising:
a defibrillator including
a body,
a pair of disposed electrodes in fixed operative connection with the body,
a trigger,
wherein the trigger is movably mounted in operative connection with the body,
a hammer,
wherein the hammer is movably mounted in operative connection with the body and the trigger,
a circuit,
wherein the circuit includes a piezoelectric crystal,
wherein the circuit is in electrical connection with each of the electrodes,
wherein manual movement of the trigger relative to the body is operative to cause the hammer to impart an impact strike to the crystal, wherein the strike is operative to cause the circuit to produce an electrical potential between the electrodes sufficient to provide an electrical shock to heart muscles of a patient through the electrodes in engagement with a chest of the patient,
a docking station,
wherein the docking station is configured to engage the defibrillator for storage therein, and wherein the docking station is operative to ground at least one of the electrodes when the defibrillator is engaged with the docking station.

23. Apparatus comprising:
a defibrillator including
a body, wherein the body includes a handle and a surface and
a pair of electrodes transversely disposed on the surface and in fixed operative connection with the body,
wherein each of the electrodes
is externally accessible on the body, and
includes a contact face surface configured to externally contact a chest of a patient,
wherein the face surfaces of the electrodes extend in a common plane
a trigger,
wherein the trigger is movably mounted in operative connection with the body and extends transversely intermediate of the electrodes,
a hammer,
wherein the hammer is movably mounted in operative connection with the body and is in operative connection with the trigger,
a circuit,
wherein the circuit includes a piezoelectric crystal,
wherein the circuit is in electrical connection with each of the electrodes,
wherein the trigger, hammer and circuit are within the handle, and
wherein manual movement of the trigger in an actuating direction that is perpendicular to the common plane is operative to cause the hammer to impart an impact strike to the crystal, wherein the strike is operative to cause the circuit to produce an electrical potential between the electrodes sufficient to provide an electrical shock to heart muscles of the patient through the face surfaces of the electrodes each of which is in direct contact with the chest of the patient.

24. The apparatus according to claim 23 wherein the electrodes are fixed relative to the body and are disposed apart a fixed transverse distance.

25. The apparats according to claim 23 wherein the actuating direction of the trigger is toward the chest of the patient.

\* \* \* \* \*